United States Patent
LaVon et al.

(10) Patent No.: US 10,299,970 B2
(45) Date of Patent: May 28, 2019

(54) REFASTENABLE ARTICLES COMPRISING FOLDED FASTENING TAB MEMBERS

(71) Applicant: The Procter & Gamble Company, Cincinnati, OH (US)

(72) Inventors: Gary Dean LaVon, Liberty Township, OH (US); Jacob Alan Barnhorst, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/205,642

(22) Filed: Mar. 12, 2014

(65) Prior Publication Data

US 2014/0276525 A1    Sep. 18, 2014

Related U.S. Application Data (60) Provisional application No. 61/787,416, filed on Mar. 15, 2013.

(51) Int. Cl.
| | |
|---|---|
| *A61F 13/15* | (2006.01) |
| *A61F 13/62* | (2006.01) |
| *A61F 13/64* | (2006.01) |
| *A61F 13/56* | (2006.01) |

(52) U.S. Cl.
CPC .......... *A61F 13/622* (2013.01); *A61F 13/565* (2013.01); *A61F 13/64* (2013.01); *A61F 13/5655* (2013.01)

(58) Field of Classification Search
CPC .. A61F 13/64; A61F 13/49061; A61F 13/622; A61F 13/55115; A61F 13/551; A61F 13/565; A61F 13/5655; A61F 13/5622; A61F 13/5635; A61F 13/5638; A61F 13/5644; A61F 13/62; A61F 13/625; A61F 13/627
See application file for complete search history.

(56) References Cited

U.S. PATENT DOCUMENTS

| | | | |
|---|---|---|---|
| 4,869,724 A | 9/1989 | Scripps | |
| 5,156,793 A | 10/1992 | Buell et al. | |
| 5,167,897 A | 12/1992 | Weber et al. | |
| 5,695,488 A * | 12/1997 | Sosalla | 604/385.24 |
| 6,454,752 B1 | 9/2002 | Huang et al. | |

(Continued)

FOREIGN PATENT DOCUMENTS

| | | |
|---|---|---|
| CA | 2 787 113 A1 | 6/2007 |
| GB | 1441567 A | 7/1976 |

(Continued)

OTHER PUBLICATIONS http://www.merriam-webster.com/dictionary/belt; Dec. 10, 2015.*

(Continued)

*Primary Examiner* — Bradley H Philips
(74) *Attorney, Agent, or Firm* — Richard L. Alexander (57) ABSTRACT

Absorbent articles of the disclosure may comprise first and second belt webs, a folded fastening tab member comprising first and second fastening elements, first and second landing zones, and laterally opposing permanent side seams directly or refastenably joining the first and second belt webs. The fastening tab member may be joined to the first and second fastening elements. And, the absorbent article may be packaged in refastenably closed form.

13 Claims, 5 Drawing Sheets

(56) References Cited

U.S. PATENT DOCUMENTS

| | | | |
|---|---|---|---|
| 6,524,294 B1 | 2/2003 | Hilston | |
| 6,579,275 B1 | 6/2003 | Pozniak | |
| 6,635,135 B2* | 10/2003 | Kuen | A61F 13/15747 |
| | | | 156/199 |
| 7,455,665 B2 | 11/2008 | Wendelstorf et al. | |
| 7,527,617 B2 | 5/2009 | Shimaida et al. | |
| 7,708,857 B2 | 5/2010 | Ukegawa | |
| 7,799,162 B2 | 9/2010 | Wood et al. | |
| 7,862,549 B2 | 1/2011 | Desai et al. | |
| 8,012,296 B2 | 9/2011 | Ukegawa | |
| 8,177,766 B2 | 5/2012 | Mansfield | |
| 8,227,071 B2 | 7/2012 | Wood et al. | |
| 8,235,964 B2 | 8/2012 | Perneborn | |
| 8,287,512 B2 | 10/2012 | Gabriele | |
| 8,372,052 B2 | 2/2013 | Popp et al. | |
| 8,579,876 B2 | 11/2013 | Popp et al. | |
| 8,632,515 B2 | 1/2014 | Popp et al. | |
| 2002/0123730 A1* | 9/2002 | Popp et al. | 604/385.03 |
| 2003/0018315 A1 | 1/2003 | Popp | |
| 2003/0078558 A1 | 4/2003 | Karami et al. | |
| 2003/0135184 A1* | 7/2003 | Van Gompel | A61F 13/15756 |
| | | | 604/385.01 |
| 2003/0167049 A1 | 9/2003 | Gibbs | |
| 2004/0138639 A1 | 7/2004 | Ito et al. | |
| 2004/0181200 A1 | 9/2004 | Desai et al. | |
| 2005/0010188 A1* | 1/2005 | Glaug | A61F 13/15577 |
| | | | 604/396 |
| 2006/0108054 A1 | 5/2006 | Ukegawa | |
| 2006/0241559 A1* | 10/2006 | Buhrow et al. | 604/385.09 |
| 2009/0043275 A1* | 2/2009 | Perneborn | A61F 13/15756 |
| | | | 604/391 |
| 2010/0292663 A1 | 11/2010 | LaVon et al. | |
| 2011/0092947 A1 | 4/2011 | Kline et al. | |
| 2012/0065607 A1 | 3/2012 | Konig | |
| 2012/0070254 A1 | 3/2012 | Hamada | |
| 2013/0138073 A1 | 5/2013 | Horn et al. | |
| 2014/0005020 A1 | 1/2014 | LaVon | |
| 2014/0276525 A1 | 9/2014 | LaVon et al. | |

FOREIGN PATENT DOCUMENTS

| | | |
|---|---|---|
| JP | 2012-050883 | 3/2012 |
| WO | WO-2011/091110 | 7/2011 |
| WO | WO-2012/095739 | 7/2012 |

OTHER PUBLICATIONS http://www.formaxprinting.com/blog/2010/08/printing-lingo-what-is-a-z-fold/.*

International Search Report and Written Opinion, PCT/US2014/028475, date of mailing May 23, 2014.

* cited by examiner

REFASTENABLE ARTICLES COMPRISING FOLDED FASTENING TAB MEMBERS

CROSS REFERENCE TO RELATED APPLICATION

This application claims the benefit of U.S. Patent Application Ser. No. 61/787,416, filed on Mar. 15, 2013, the entire disclosure of which is hereby incorporated by reference.

BACKGROUND

Disposable absorbent articles in pant form may comprise an elasticized belt that encircles the wearer's waist and may form the waist edge about the entire pant. A central chassis may be joined to the elasticized belt, usually on the inside thereof, with its ends disposed at locations in the front and rear waist regions somewhat below the waist edges of the elasticized belt. This configuration is sometimes known as a "belt" or "balloon" configuration (hereinafter, "belt" configuration). An example of this type of configuration is currently manufactured and sold in Asia by The Procter & Gamble Company under the trademark PAMPERS, and also by Unicharm Corporation under the trademark MAMY POKO.

For purposes of ease of use it may be desired that the pant have a refastenable feature for enabling ease of opening and reclosing of the belt-like structure. This may be accomplished by incorporating for example mechanical fastening elements into the structure of the absorbent article as part of the belt-like structure, the central chassis, other elements of the article and/or combinations thereof. The refastenable feature may help maintain and/or establish the leg openings and the waist opening. Although some currently manufactured belt configuration pants include refastenable features they may be considered to be too complex to produce—especially at high production speeds, and too complex to use. And, some may be considered to have a rough or unfinished appearance.

The present disclosure reveals improvements to the structural design and process for making of disposable absorbent pants having a belt configuration comprising fastening components for forming a refastenable feature compatible with high speed manufacturing.

Particularly, the present disclosure reveals advantages of folding the fastening tabs. For instance, a folded fastening tab (e.g., 210) enables a narrower footprint of the absorbent article via an increased pathlength of the fastening tab's carrier layer and hooks because the extended carrier layer acts as a folded belt. The narrow footprint makes for a neater looking product. Also, this helps drive smaller packaging and portability and convenience. Further, this reduces the need to fold or tuck the belt.

Another advantage of folding the fastening tab is that it can be made of a different more expensive, higher stretch material than the rest of the belt. This enables the belt to be lower stretch or nonelastic. The fastening tab can be a much higher basis weight material than the belt, which is cost effective and which improves fastening performance by providing a cushion for the fastening elements, which may be made of a stiffer material. The more expensive material (that the fastening tab could be made of) could be a film versus a nonwoven to enable alternative forms of fastening like adhesives, cohesive, and the like. Another material that may be used for fabricating the fastening tab may include a film-strand laminate.

Further, folding the fastening tab enables disposition of the fastening elements more on the front or back on belts without folding either of the belts. For example, the fastening tabs may be back-biased on larger sizes for older wearers to avoid having the child remove or open the fastener. Alternatively, the fastening tabs may be front-biased for younger kids who lay on their backs to get changed.

DEFINITIONS

"Fastening component" refers to the fastening elements that define an area of refastenable attachment. The fastening components enable refastening of the absorbent article to reconfigure the waist and leg openings into a closed configuration until the fastening components are separated. A fastening component may comprise one or more refastenable fastening elements, e.g., hooks, loops, bulbs, mushrooms, arrowheads, balls on stems, buttons, snaps, refastenable cohesives, selective refastenable adhesives, etc. A fastening component may be opened and subsequently reclosed, reliably, without destroying the fastening component. A fastening component comprises those elements of a fastening system that form the area of attachment via direct surface-to-surface contact forming a refastenable closure. For the purpose of clarity, surface-to-surface contact encompasses contact between a surface of a hook material and a surface of a loop material, for example. For instance, a tab member joined to a backsheet would not be a fastening member as discussed. The fastening component may be the hooks or the loops that are joined to the tab and connect with the other fastening components or a portion of an absorbent article.

"Elastic" or "elastomeric" refers to the property of an extensible material (or a composite of multiple materials) that can extend, without substantial rupture or breakage, to a strain of 100%, with a set less than or equal to 10% of the elongation. An elastic material is considered elastically extensible.

"Lateral"—with respect to a pant and its wearer, refers to the direction generally perpendicular with the wearer's standing height, or the horizontal direction when the wearer is standing. "Lateral" is also the direction generally perpendicular to a line extending from the midpoint of the front waist edge to the midpoint of the rear waist edge.

"Longitudinal"—with respect to a pant and its wearer, refers to the direction generally parallel with the wearer's standing height, or the vertical direction when the wearer is standing. "Longitudinal" is also the direction generally parallel to a line extending from the midpoint of the front waist edge to the midpoint of the rear waist edge.

"Pant" (also referred to as "disposable training pant," "training pant," "incontinence pant," and "pull-on pant-type diaper") refers to disposable absorbent articles having a continuous perimeter waist opening and continuous perimeter leg openings designed for infant, child, or adult wearers (hereafter "wearer"). A pant may be configured with a continuous or closed waist opening and at least one continuous or closed leg opening prior to the pant being applied to the wearer. A pant may be pre-formed by any suitable technique including, but not limited to, joining together portions of the absorbent article using any refastenable and/or permanent closure member(s) (e.g., seams, heat bonds, pressure welds, adhesives, cohesive bonds, mechanical fasteners, etc.). A pant may be preformed anywhere along its circumference in the waist region (e.g., side fastened, front waist fastened, rear waist fastened). Example pants and pant configurations are disclosed in U.S. Pat. Nos. 5,246,433, 5,569,234, 6,120,487, 6,120,489, 4,940,464, 5,092,861, 5,897,545, 5,957,908, and U.S. Pat. Publ. No. 2003/0233082.

"Side edge seam" refers to a given side edge wherein a portion of the side edge, or region adjacent the side edge, in the front waist region is joined to a portion of the same side edge, or region adjacent the side edge, in the rear waist region to define closed, encircled leg openings and a closed waist opening.

Figure 1:
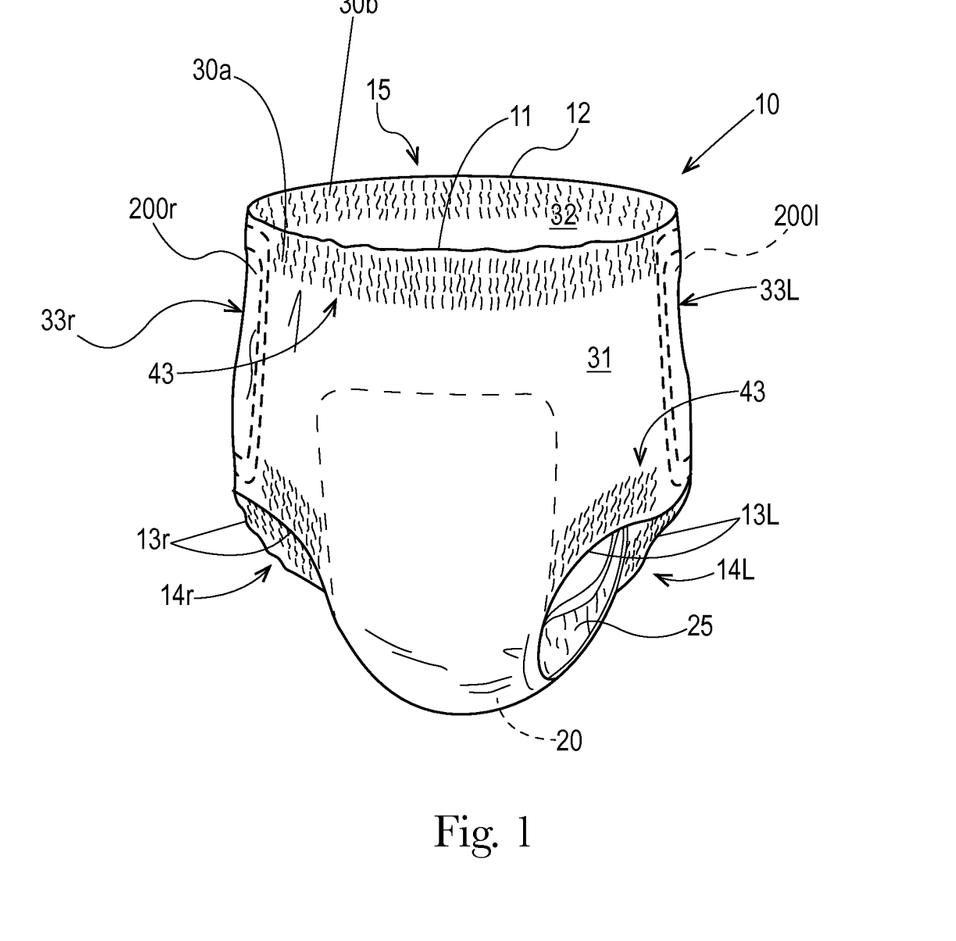
FIG. 1 is simplified perspective view of a disposable absorbent pant.

FIG. 1 is a general simplified perspective depiction of a disposable absorbent pant 10 having a belt configuration. Pant 10 may include a central chassis 20 and an elasticized belt 30. Elasticized belt 30 may be elastically extensible in the lateral direction, providing elastic stretchability for ease of donning, and a snug and comfortable fit following donning Central chassis 20 may include a wearer-facing, liquid permeable topsheet (not specifically shown in FIG. 1), an outer- or garment-facing backsheet (not specifically shown in FIG. 1) and an absorbent core (not specifically shown in FIG. 1) sandwiched or enveloped between the topsheet and backsheet. A pair of laterally opposing, longitudinally extending barrier cuffs 25 also may be included with the central chassis in a crotch region thereof, disposed adjacent to the topsheet. Generally the central chassis and barrier cuffs may have any construction and components, including leg cuff structures, suitable for disposable diapers, training pants, and adult incontinence pants, such as, but not limited to, those described in U.S. provisional patent application No. 61/480,663 and application(s) claiming priority thereto. Elasticized belt 30 may have a front portion 31 and a rear portion 32. Front and rear portions 31, 32 may be joined together at respective left and right side edge seams 33l, 33r. Elasticized belt 30 may form front and rear waist edges 11, 12 defining waist opening 15, and at least portions of left and right leg opening edges 13l, 13r of the pant 10. The disposable absorbent pant 10, and more particularly, the elasticized belt 30 may comprise fastening components 200l and 200r for creating a refastenable feature.

Figure 2:
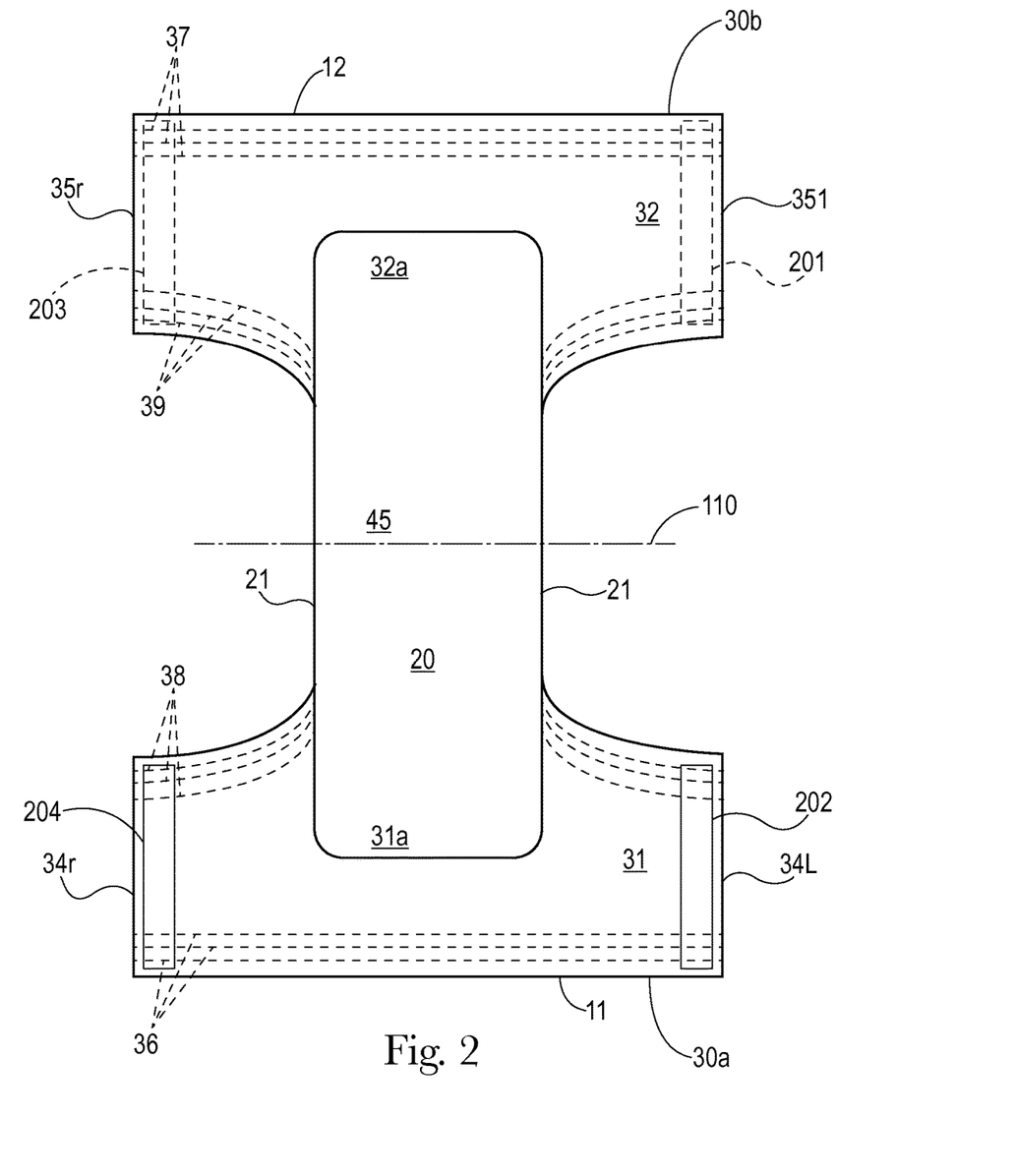
FIG. 2 is a simplified plan view of a precursor structure of a disposable absorbent pant, shown with inner or wearer-facing surfaces upward.

FIG. 2 is a simplified plan view of the precursor structure of the pant 10 shown in FIG. 1, shown prior to joining of front and rear portions 31, 32 along their respective side edges 34l, 35l and 34r, 35r. Front region 31a, including front portion 31, and rear region 32a, including rear portion 32, may each include anywhere from 25 percent to 40 percent of the overall longitudinal length of the precursor structure; correspondingly, a crotch region 45 may include anywhere from 20 percent to 50 percent of the overall longitudinal length of the precursor structure, with at least a portion thereof lying at lateral axis 110. To form pant 10, the precursor structure may be folded along lateral axis 110 to bring front and rear regions 31a, 32a, and front and rear portions 31, 32 together such that their side edges 34l, 35l and 34r, 35r, respectively, may be joined at side edge seams 33l, 33r (as shown in FIG. 1). The embodiment shown in FIG. 2 comprises fastening elements 201-204 that may be refastenably joined together. Particularly, fastening elements 201 and 203 may be hook elements that join with fastening elements 202 and 204, respectively. Fastening elements 201 and 203 are shown on an exterior surface of the elasticized belt 30, but they may also be placed on an interior surface of the elasticized belt 30. Fastening elements 202 and 204 may be a discrete member of loop elements or may be an area of loop elements that is part of a nonwoven sheet lining the interior (as shown) or exterior of the elasticized belt. In another embodiment, fastening elements 201 and 203 may be loop elements and fastening elements 202 and 204 may be hook elements. Additional embodiments of fastening elements are described and illustrated in FIGS. 4-6.

It is understood that when the fastening elements 201-204 mate interior surface to interior surface of the elasticized belt 30, a flange seam is formed. But, when the fastening elements 201-204 mate interior surface to exterior surface of the elasticized belt 30, an overlap seam is formed, as illustrated in FIG. 1. The fastening elements 201-204 may be fastened during the manufacturing process and/or fastened in the package prior to use by the wearer or caregiver (i.e., the pant may be sold in "closed form"). Alternatively, the pant may be sold in "open form," where the fastening elements 201-204 are not joined in the package.

Still referring to FIG. 2, one or both of front and rear portions 31, 32 may include at least a first elastic member 36, 37 disposed nearer the waist edges 11, 12 and at least a second elastic member 38, 39, disposed nearer the leg opening edges 13l, 13r. As suggested in FIG. 2, one or a plurality of waist elastic members 36, 37 may be disposed in a substantially straight lateral orientation, and one or a plurality of leg elastic members 38, 39 may be disposed along curvilinear paths to provide hoopwise elastic stretch about the leg openings 13l, 13r (as shown in FIG. 1). For purposes of manufacturing a pant having a neat appearance as will be described below, it may be desired that leg elastic members 38, 39 terminate proximate the respective longitudinal edges 21 of chassis 20.

Elastic members 36, 37, 38 and 39 may be in the form of film or sections or strips thereof, strips, ribbons, bands, scrims or strands of circular or any other cross-section, formed in any configuration of any elastomeric material such as described in, for example, co-pending U.S. application Ser. Nos. 11/478,386 and 13/331,695, and U.S. Pat. No. 6,626,879. A suitable example is LYCRA HYFIT strands, a product of Invista, Wichita, Kans.

The elasticized belts and rear region of the pant may be in a number of configurations as described and illustrated in FIGS. 3A-C and 4A-k of U.S. Ser. No. 61/666,065, filed on Jun. 29, 2012, titled DISPOSABLE ABSORBENT REFASTENABLE PANTS AND METHODS FOR MANUFACTURING THE SAME. Further, the absorbent articles of this disclosure may be manufactured in accordance with the descriptions and illustrations of U.S. Ser. No. 61/666,065 (see, for example, FIGS. 5-10C of the '065 application).

Figure 3:
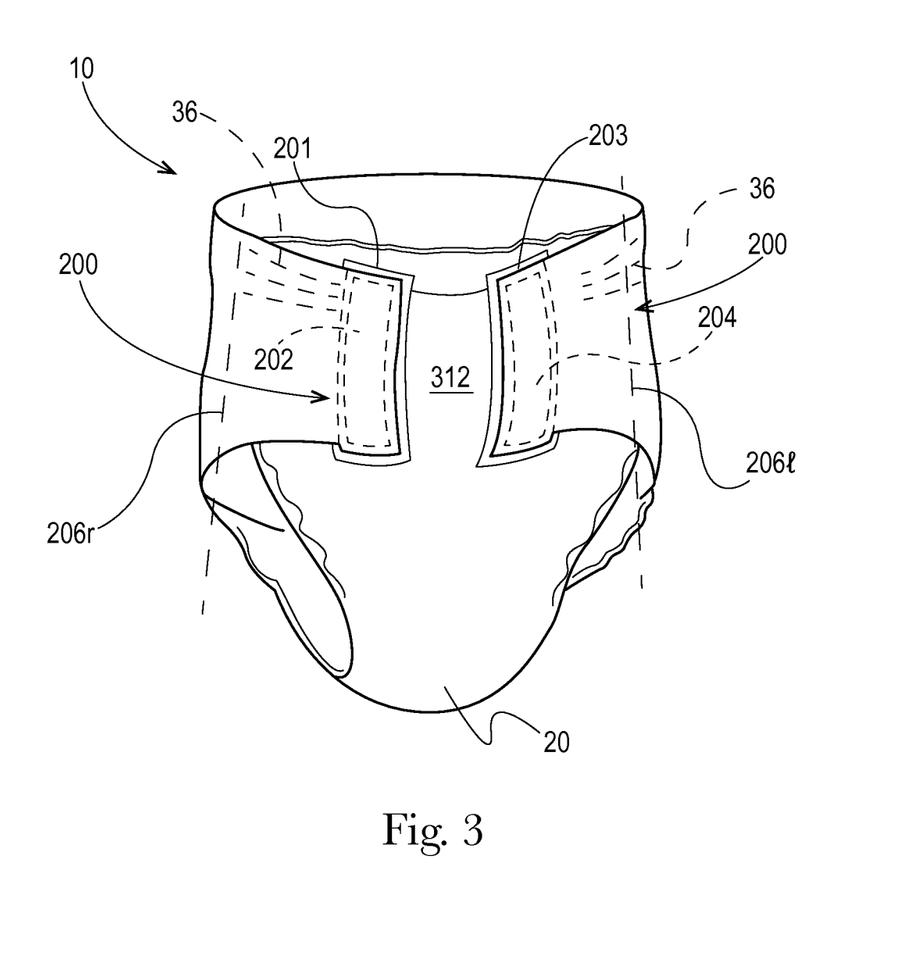
FIG. 3 is simplified perspective view of a disposable absorbent pant.

Referring to FIG. 3, in one embodiment, the fastening elements 201-204 may, when joined to form the leg and waist openings 14 and 15, respectively, be disposed or formed within the front region 31a of the pant 10 to improve access to the fastening components 200. When the fastening elements are joined and the leg and waist openings are formed, the front region 31a may be considered the area of the pant 10 forward of each of the hip axis 206 (the axis that represents the middle of the wearer's hip when worn). It is noted that loop type fastening elements 201 and 203 may merely be disposed on or form a portion of the front region 31a, to which the first hook-type fastening elements 202 and 204 may be fastened with. Improving access to the fastening components 200 by orienting them such that they are in the front region 31a when joined may make opening and refastening of the pant 10 significantly easier for a caregiver and allow front waist region to front region 31a fastening, making the pant 10 changing or pant 10 checking process easier for the caregiver when the wearer is standing in front of the caregiver (e.g., face-to-face) or when the wearer is laying on his or her back. In addition, fastening of the fastening components 200 in the front region 31a of a pant 10 or diaper is also familiar to the caregiver since this is similar to tape-style diapers.

The ability to open and refasten the pants offers convenience to the caregiver. For instance, it might be more convenient to apply the pants as a traditional tape-style diaper when away from home or when it is inconvenient to remove the clothing and/or shoes of the wearer. Because it is difficult to predict when the wearer will need to be changed and, therefore, when a particular mode of application will be needed, it would be beneficial to provide a pant that is adaptable to being applied either as a traditional tape-style diaper or as a disposable training pant. In addition, a product that may be applied like a traditional tape-style diaper or a disposable training pant also permits inspection of the interior of the product without having to slide the product down the legs of the wearer. The pants of the present disclosure provide dual functionality with regard to application and removal while enabling the easy wrapping up and disposal of the used pants.

In various embodiments, each of the fastening components 200 may be joined directly or indirectly to the pant 10 by any suitable methods, such as adhesive bonding, sonic bonding, pressure bonding, thermal bonding or combinations thereof, for example. Some suitable examples of fastening systems and/or the fastening components 200 are discussed in U.S. Pat. Nos. 3,848,594, 4,662,875, 4,846,815, 4,894,060, 4,946,527, 5,151,092, 5,221,274, 6,251,097, 6,669,618, 6,432,098, 7,101,359, and 7,407,468.

Figure 4:
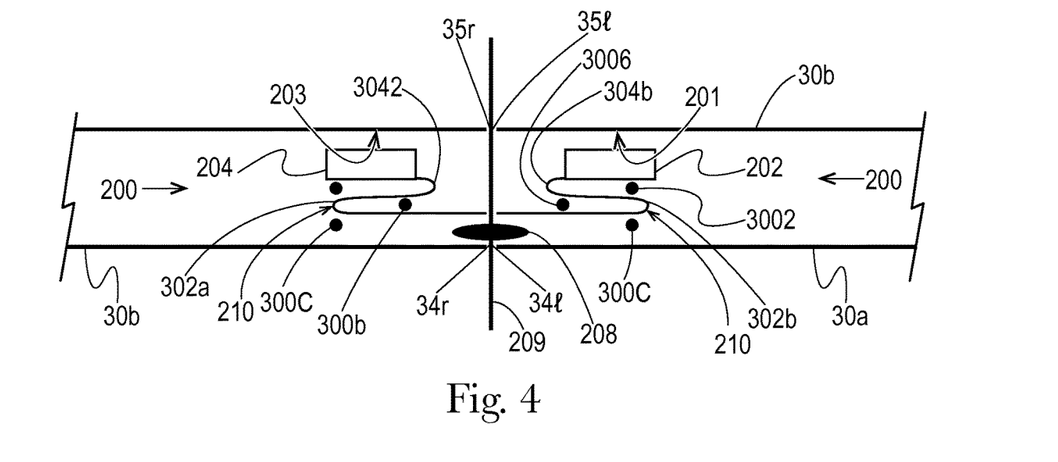
FIGS. 4-6 are simplified, schematic cross-section views of portions of a multilayer web comprising fastening components.

FIG. 4 illustrates the formation of two articles folded over a lateral axis (e.g., 110 in FIG. 2) to form a pants, e.g., pant 10-1 and pant 10-2, wherein only a portion of each is shown. In this embodiment, which is only one embodiment of the present disclosure, each of the pants 10-1 and 10-2 comprise front belts 30a that extend from a first side edge 34r and 34l, respectively, to a laterally opposing second side edges (not shown) and form portions of laterally opposing permanent side edge seams 208. Also for each of the pants 10-1 and 10-2, the rear belts 30b extend from adjacent first side edges 35r and 35l, respectively, to an area adjacent the opposing second side edges (not shown) and do not form a portion of the laterally opposing permanent side edge seams 208. The pants 10-1 and 10-2 further comprise fastening tab members 210 disposed between the front and rear belts 30a and 30b. The fastening tab members 210 of this embodiment are permanently joined to a wearer facing surface of the front belt and comprise first and second fastening elements 202 and 204 disposed between the fastening tab member 210 and the rear belts 30b and are capable of being refastenably engaged with a wearer facing surface of the rear elasticized belts 30b. In this embodiment, the fastening tab member 210 is double folded (laterally inward, then laterally outward) such that the fastening tab members 210 comprises first folds 302a and 302b, and second folds 304a and 304b. The web making up the fastening tab members 210 may be folded prior to being joined to the elasticized belts 30 (for this embodiment, as well as the embodiments of FIGS. 5 and 6 also, and generally).

Temporary bonds 300a-c may used to control the web and/or to keep the fastening tab members 210 tight against the rear belts 30b. Temporary bonds 300a-c may each vary in bond strength (e.g., 300a may be weaker than 300b, which may be weaker than 300c) or they may all be the same strength. Temporary bonds 300a-c may be formed by the adhesives disclosed in Ser. No. 12/794,130, titled METHOD FOR MAINTAINING A FASTENER IN A FOLDED CONFIGURATION, filed on Jun. 4, 2010. Temporary bonds may also be used on the webs making up the fastening tab members 210 of the embodiments of FIGS. 5 and 6, and generally. The fastening components 200 may comprise second fastening elements 201 and 203 formed in or disposed on the rear belts 30b. In this configuration, the web making up the fastening tab member 210 is disposed between the fastening elements 202 and 204 and the front belt 30a.

In an alternative embodiment of the present disclosure (not shown), an identical embodiment to FIG. 4, except that fastening tab member 210 may be attached to the rear belt 30b and the fastening elements 202 and 204 may be capable of refastenably engaging with the front elasticized belt 30a.

Figure 5:
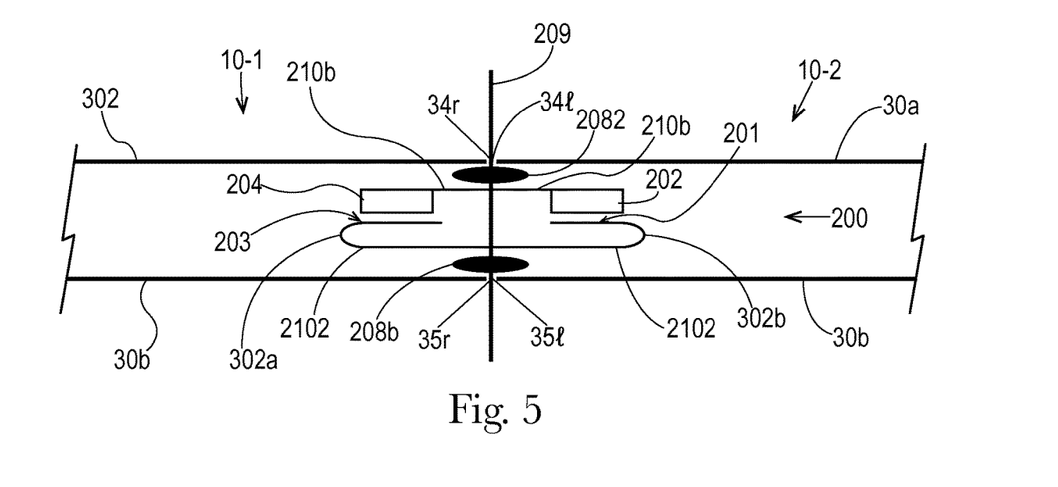

FIG. 5 illustrates the formation of two articles folded over a lateral axis (e.g., 110 in FIG. 2) to form a pants, pant 10-1 and pant 10-2, wherein only a portion of each is shown. In this embodiment, which is only one embodiment of the present disclosure, each of the pants 10-1 and 10-2 comprise rear belts 30b that extend from a first side edge 35r and 35l, respectively, to a laterally opposing second side edges (not shown) and form portions of laterally opposing permanent side edge seams 208b. Also, for each of the pants 10-1 and 10-2, the front belts 30a extend from adjacent a first side edges 34r and 34l, respectively, to an area adjacent the opposing second side edges (not shown) and form a portion of the laterally opposing permanent side edge seams 208a. The articles further comprise fastening tab members 210a permanently joined to a wearer facing surface of the rear belts 30b. In this embodiment, the fastening tab member 210a is single folded such that the fastening tab member 210 comprises first folds 302a and 302b. The articles also comprise first fastening elements 202 and 204 disposed on fastening tab member 210b (permanently joined to a wearer facing surface of the front belts 30a) and are capable of being refastenably engaged with the fastening tab members 210a. The fastening components 200 may comprise second fastening elements 201 and 203 formed in or disposed on the fastening tab members 210a. In this configuration, the web making up the fastening tab members 210a is disposed between the fastening elements 202 and 204 and the rear belt 30b.

In an alternative embodiment of the present disclosure (not shown), an identical embodiment to FIG. 5, except that fastening tab member 210a may be attached to front belt 30a and fastening tab member 210b may be attached to rear belt 30b.

Figure 6:
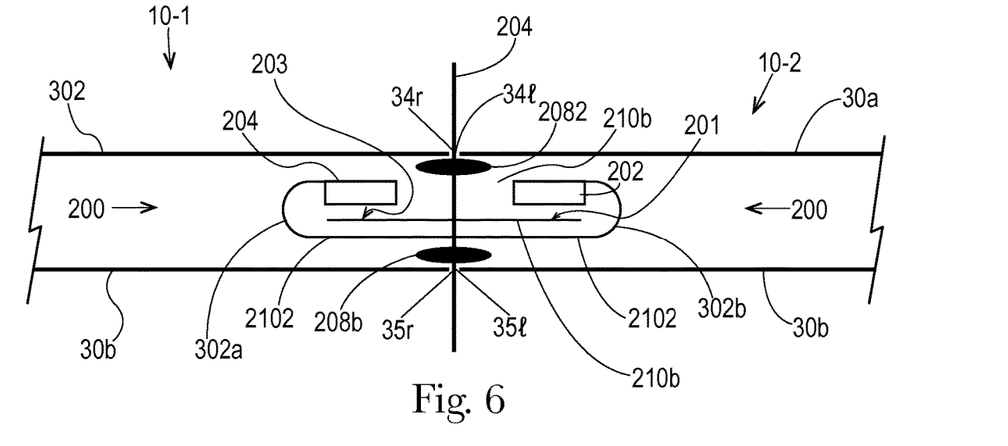

FIG. 6 illustrates the formation of two articles folded over a lateral axis (e.g., 110 in FIG. 2) to form a pants, pant 10-1 and pant 10-2, wherein only a portion of each is shown. In this embodiment, which is only one embodiment of the present disclosure, each of the pants 10-1 and 10-2 comprise rear belts 30b that extend from a first side edge 35r and 35l, respectively, to a laterally opposing second side edges (not shown) and form portions of laterally opposing permanent side edge seams 208b. Also, for each of the pants 10-1 and 10-2, the front belts 30a extend from adjacent a first side edges 34r and 34l, respectively, to an area adjacent the opposing second side edges (not shown) and form a portion of the laterally opposing permanent side edge seams 208a. The articles further comprise fastening tab members 210a permanently joined to a wearer facing surface of the rear belts 30b. In this embodiment, the fastening tab member 210a is single folded such that the fastening tab member 210 comprises first folds 302a and 302b. The articles also comprise first fastening elements 202 and 204 disposed on fastening tab member 210a and are capable of being refastenably engaged with the fastening tab member 210b (permanently joined to a wearer facing surface of the front belts 30a). The fastening components 200 may comprise second fastening elements 201 and 203 formed in or disposed on the fastening tab members 210b. In this configuration, the web making up the fastening tab members 210a is disposed between the fastening elements 201 and 203 and the front belt 30a.

In an alternative embodiment of the present disclosure (not shown), an identical embodiment to FIG. 6, except that fastening tab member 210a may be attached to front belt 30a and fastening tab member 210b may be attached to rear belt 30b. For example in FIG. 6 the folded portion of the web attached to the rear belt is disposed between the tab member 203 and the front belt and being joined to the wearer facing surface of the tab member. In FIG. 5 the folded portion of the web attached to the rear belt is disposed between the tab member and the rear belt and attached to the garment facing surface of the tab member Each of the embodiments illustrated by FIGS. 4-6 requires a folded fastening tab member. Folding the fastening tab member one or more times allows for extra fastening tab material to be used for the purpose of making up a greater part of the waist circumference. So, front and back belt material having less elasticity may be used in combination with a folded fastening tab member having higher stretch capacity. Thus, the front and back belts may be a different material than the fastening tab member. For example, the belts may be stranded elastic/nonwoven laminates, while the fastening tab members may be film/nonwoven laminates or film/strand laminates.

For each of the embodiments illustrated by FIGS. 4-6, as well as the disclosed alternate embodiments of these Figs., it should be understood that the belts 30a and 30b may be formed in accordance with U.S. Ser. No. 61/646,999, filed on May 15, 2012. Further, the methods of manufacture and the resulting texture as disclosed by U.S. Ser. Nos. 61/647,061, 61/647,071, 61/647,078, each filed on May 15, 2012, may be used. And, the stress, strain, and spacing of the belt elastics may be done as disclosed in U.S. Ser. No. 61/598,012, filed Feb. 13, 2012.

Also, it should be understood that these articles may comprise the cuffs disclosed in U.S. Ser. No. 13/457,521, filed Apr. 27, 2012, and may have graphics in accordance with U.S. Ser. Nos. 61/646,953 and 61/646,979, each filed on May 15, 2012. And, it may be desirable to use the hot air seaming processes, as well as the article forming processes disclosed in U.S. Pat. No. 6,248,195 and U.S. Ser. Nos. 12/795,021, 13/401,907, and 13/402,056 for seaming and forming the refastenable pants disclosed in each of the embodiments illustrated by FIGS. 4-6, as well as the disclosed alternate embodiments of these Figs. as these embodiments are particularly good for producing in excess of 1000 articles per minute due to their simplicity. The majority of the article elements including elastic elements are formed continuously in the machine direction. In addition, such a process enables introduction and bonding of refastenable elements to these continuous machine direction sub structures at high speed while maintaining accuracy of placement and ensuring integrity which is key to the products functionality and appearance.

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All documents cited in the Detailed Description of the Invention are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is, therefore, intended that the scope of the invention is limited only by the appended claims and equivalents thereof.

What is claimed is:

1. An absorbent article comprising:
a first belt having laterally opposed side edges, wherein the first belt comprises a first continuous nonwoven layer extending between the laterally opposed side edges of the first belt;
wherein the first belt comprises a first plurality of elastic elements adjacent to a waist opening of the absorbent article, and wherein the first plurality of elastic elements are disposed substantially parallel with a transverse axis of the absorbent article;
wherein the first belt comprises a second plurality of elastic elements adjacent to a portion of leg openings of the absorbent article;
a second belt having laterally opposed side edges, wherein the second belt comprises a second continuous nonwoven layer extending between the laterally opposed side edges of the second belt;
wherein the second belt comprises a third plurality of elastic elements adjacent to the waist opening of the absorbent article, and wherein the third plurality of elastic elements are disposed substantially parallel with the transverse axis of the absorbent article;
wherein the second belt comprises a fourth plurality of elastic elements adjacent to a portion of leg openings of the absorbent article;
a first folded fastening tab member comprising no greater than a single fold line, wherein the first folded fastening tab member comprises a first plurality of hook elements;
a second folded fastening tab member comprising no greater than a single fold line, wherein the second folded fastening tab member comprises a second plurality of hook elements;
laterally opposing permanent side seams of the first belt joining the laterally opposed side edges of the first belt with the first and second fastening tab members;

a third fastening tab member and a fourth fastening tab member;

laterally opposing permanent side seams of the second belt joining the laterally opposed side edges of the second belt with the third and fourth fastening tab members;

laterally opposing refastenable side seams formed by engagement of the first and second plurality of hooks joined to the third and fourth fastening tab members;

wherein the article is packaged in refastenably closed form; and wherein each of the first, second, third, and fourth pluralities of elastics overlap at least a portion of one of the first and second folded fastening tab members.

2. The article of claim 1, wherein the first and second pluralities of hooks engage into loops secured to the third and fourth fastening tab members.

3. The article of claim 1, wherein the first and second pluralities of hooks engage into a nonwoven surface of the third and fourth fastening tab members.

4. The article of claim 3, wherein the nonwoven surface is a wearer facing surface that the first and second pluralities of hooks engage into.

5. The article of claim 1, wherein the first and second belts are joined to a center chassis.

6. The article of claim 5, wherein the center chassis comprises a core.

7. The article of claim 6, wherein the second and fourth pluralities of elastics terminate prior to the core.

8. The article of claim 1, wherein the first and second pluralities of hooks are discrete members joined to the first and second folded fastening tab members.

9. The article of claim 8, wherein the first and second pluralities of hooks are joined to a garment-facing surface of the first and second folded fastening tab members.

10. The article of claim 1, wherein third and fourth fastening tab members are thermally bonded to the second belt.

11. The article of claim 10, wherein the third and fourth fastening tab members are not folded.

12. The article of claim 10, wherein portions of the third and fourth fastening tab members are disposed between portions of the first and second fastening tab members, respectively.

13. The article of claim 10, wherein loops are joined to a wearer-facing surface of the third and fourth fastening tab members.

* * * * *